United States Patent [19]

Sigl

[11] 4,417,938
[45] Nov. 29, 1983

[54] PRODUCING AN ELASTICIZED GARMENT UTILIZING AN ARTICULATED CONVEYOR

[75] Inventor: Wayne C. Sigl, Winnebago County, Wis.

[73] Assignee: Kimberly-Clark Corporation, Neenah, Wis.

[21] Appl. No.: 325,784

[22] Filed: Nov. 30, 1981

[51] Int. Cl.³ .............................................. B32B 31/08
[52] U.S. Cl. ..................................... 156/270; 156/164; 156/229; 156/285; 156/324; 156/522; 156/497; 198/364; 198/792; 425/336; 425/370; 425/396
[58] Field of Search ............... 156/163, 164, 229, 204, 156/205, 469, 470, 474, 459, 471, 583.7, 285, 270, 324, 522, 497; 198/364, 792; 493/410, 411, 418, 4 R, 463; 425/336, 369, 370, 396

[56] References Cited

U.S. PATENT DOCUMENTS

| 771,677 | 10/1904 | Squires | 425/396 |
|---|---|---|---|
| 2,518,565 | 8/1950 | Nicolle | 425/396 |
| 2,534,054 | 12/1950 | Parkes | 198/792 |
| 3,150,576 | 9/1964 | Gewiss | 493/463 |
| 3,516,116 | 6/1970 | Wadyjenski | 425/370 |
| 3,912,573 | 10/1975 | Kunz | 156/471 |
| 4,227,952 | 10/1980 | Sabee | 156/250 |
| 4,285,747 | 8/1981 | Rega | 156/229 |
| 4,360,398 | 11/1982 | Sabee | 156/164 |
| 4,379,016 | 4/1983 | Stemmler | 156/164 |

FOREIGN PATENT DOCUMENTS

1122430  9/1960  Fed. Rep. of Germany ...... 425/396

Primary Examiner—Jerome W. Massie
Attorney, Agent, or Firm—Richard C. Ruppin

[57] ABSTRACT

A method and apparatus is disclosed for attaching a continuously moving elastic ribbon to a continuously moving web such that only selected discrete areas of a finished conformable garment fabricated from the web are elasticized. A continuously moving belt formed of plate members hinged together and engaging the continuously moving web is guided by cam means to cause adjacent plate members to fold and thereby form folds in the web. After folding of the web, the continuously moving elastic ribbon is moved into contact with areas of the web between the folds and is adhered to the web at these areas. The elastic is cut opposite the folded areas of the web corresponding to areas in the finished diaper in which it is desired not to provide elasticization. The belt means is then guided so that the plate members unfold to thereby unfold the web.

14 Claims, 7 Drawing Figures

PRODUCING AN ELASTICIZED GARMENT UTILIZING AN ARTICULATED CONVEYOR

FIELD OF THE INVENTION

This invention relates to an apparatus and method for forming conformable garments having selected discrete elasticized areas and, more particularly, to an apparatus and method for elasticizing only the leg areas of disposable diapers on a high speed production basis.

BACKGROUND OF THE INVENTION

Due to the improved fit and fluid sealing properties provided by leg elasticization, manufacturers of disposable diapers have, in recent years, developed various methods and apparatus for attaching elastic strips to the leg areas of the diapers. Because of the high speed, continuous nature of diaper manufacturing methods, virtually all of the commercially practicable processes have utilized a continuous elastic ribbon affixed to the diaper in the leg areas and subsequently cut either prior to or as a part of the severing of the continuous web into separate diapers. Typical of these processes and apparatus is that disclosed in U.S. Pat. No. 4,081,301 to Buell. This patent discloses adhering of the continuous elastic ribbon only in discrete, intermittent areas corresponding to the leg areas in a finished diaper. The ribbon and the diaper are then simultaneously cut at the waist of the diaper when the continuous web is cut into separate diapers. The drawback of this process is that it is inefficient from the material use aspect in that it leaves an unneeded length of elastic attached to the diaper. Another approach to handling the problem is disclosed in U.S. Pat. No. 4,227,952 to Sabee. In the method of this patent, the elastic ribbon is continuously applied to the web, however, before the attachment of the ribbon to the web, the latter is folded in the areas of the web corresponding to the waist areas of the finished diapers. Consequently, the elastic ribbon is attached to the web only in the leg areas of the finished diaper. The elastic ribbon is then severed at the points opposite the folded areas of the web and the web is then unfolded so that elastic is only in the leg areas of the finished diaper and the waist areas contain no unneeded elastic. The problem with this method and the apparatus used in it is that it is quite complex and difficult to operate at the high speeds required for commercial usefulness. Much of the complexity of the Sabee approach is due to the use of two separate conveyor chains each carrying a plurality of projecting members which must intermesh during the carrying out of the process.

SUMMARY OF THE INVENTION

It is a principal object of this invention to provide, for use in a high speed production process, a relatively simple, efficient method and apparatus for attaching a continuously moving elastic ribbon to a continuously moving web such that only selected discrete areas of a finished conformable garment fabricated from the web will be elasticized. In particular, it is an object of this invention to provide a method and apparatus for attaching a continuously moving elastic ribbon to a continuously moving web such that only the areas of the web corresponding to the leg areas in finished diapers will be elasticized. It is a further object of this invention to provide an elastic ribbon attached to a web such that there is elastic ribbon positioned only in selected discrete areas of a finished conformable garment or, in the case of a finished diaper, only in the leg areas.

The objectives of the invention are accomplished by providing a continuously moving articulated belt means which supports a web continuously moving with the articulated means and a means for continuously moving an elastic ribbon into engagement with the web. The articulated belt means includes a plurality of plate members and a plurality of pivotally joined hinge means connecting the plate members together. The hinge means carry roller or cam members which follow guide means as the belt means is moved. During one portion of the travel of the belt means, the cam members follow a path which maintains them in a relatively aligned position, however, during another part of the travel of the belt means, selected ones of the hinge means and cam members are diverted by the guide means to a separate path from that of the other hinge means and cam members. The plate members are thereby moved from a relatively planar, aligned position to a folded position in which the belt means is generally in an articulated condition. Prior to the articulating of the belt means, the web is brought into engagement with the belt means so that, when the articulation, occurs, the web moves with the belt means and folded pockets are formed in the web. Subsequent to the forming of the folded pockets in the web, the elastic ribbon is brought into contact with the web so that the elastic spans the fold pockets of the web and engages only the areas of the web between fold pockets. In the preferred embodiment of the invention, the elastic ribbon is then cut opposite the folded pockets of the web and the pockets become, in a finished product, the non-elasticized portion of the product. The guide means then guides the hinge means and plate members to their aligned positions to thereby unfold the belt means and remove the fold pockets in the web.

The term "elasticize" and variations of such term, as used herein, are intended to mean the producing of an elastic effect. Thus, there is elasticization if the elastic ribbon is applied to the web in a tensioned condition or if the elastic is applied to the web in a relaxed condition such that it can be subsequently extended when the finished garment is placed on a wearer.

DESCRIPTION OF THE DRAWINGS

Further objects and advantages of the invention will appear when taken in conjunction with the accompanying drawings, in which.

DETAILED DESCRIPTION OF THE INVENTION

Figure 14:
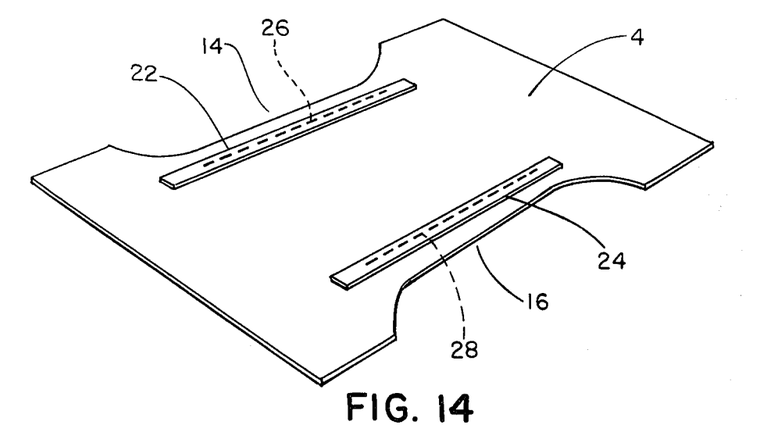
FIG. 14 is a perspective view showing the backsheet of a disposable diaper which comprises a section of the web.
Figure 15:
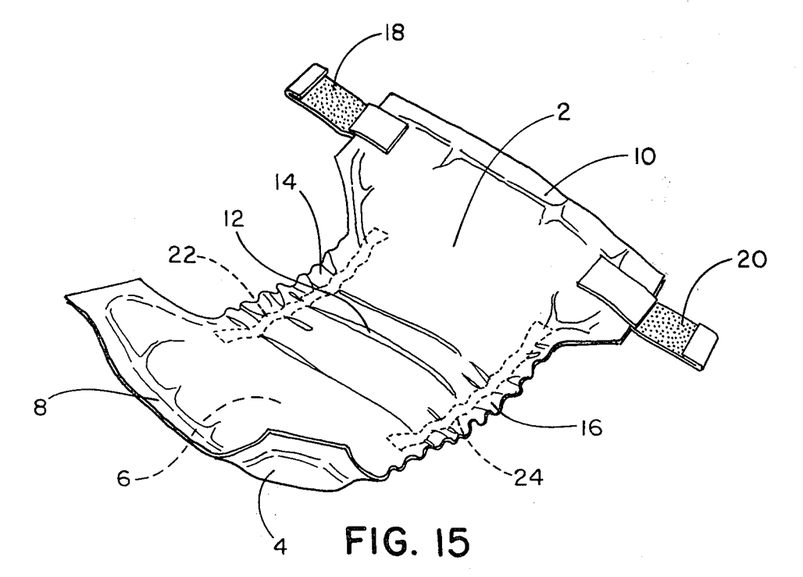
FIG. 15 is a perspective view of a finished elasticized leg disposable diaper just prior to its fitting onto a wearer.

For purposes of background, the elasticized leg disposable diaper produced by the apparatus and method of the invention will first be discussed. Referring first to FIGS. 14 and 15, there is shown in FIG. 15 a disposable diaper having a topsheet 2, a backsheet 4, an absorbent pad 6 between the topsheet 2 and the backsheet 4, a front waist area 8, a rear waist area 10, and a crotch area 12 intermediate the two waist areas. Leg areas 14 and 16 are positioned laterally of the crotch area 12 and intermediate of the waist areas 8 and 10. Waist fastening tapes 18 and 20 are bonded to the corner areas of the rear waist area 10 and are fastenable to the front waist area 8 when the diaper is fitted to a wearer to secure the diaper on the wearer. Elastic strips 22 and 24 are attached substantially parallel to the length of a diaper in the leg areas 14 and 16 respectively, as shown in FIG. 14, to elasticize the leg areas of the diaper and provide a snug fit around the legs of the wearer. In FIG. 15, the elastic strips 22 and 24 are shown in a relaxed condition in which they cause random pleating or folding of the topsheet 2 and back sheet 4.

In FIG. 14, the diaper components shown are the backsheet 4, the elastic strips 22 and 24, and adhesive lines 26 and 28 respectively attaching the elastic strips 22 and 24 to the backsheet 4. The backsheet 4 and the elastic strips 22 and 24 are shown in an extended, flat condition in which the elastic strips 22 and 24 are stretched.

Figure 1:
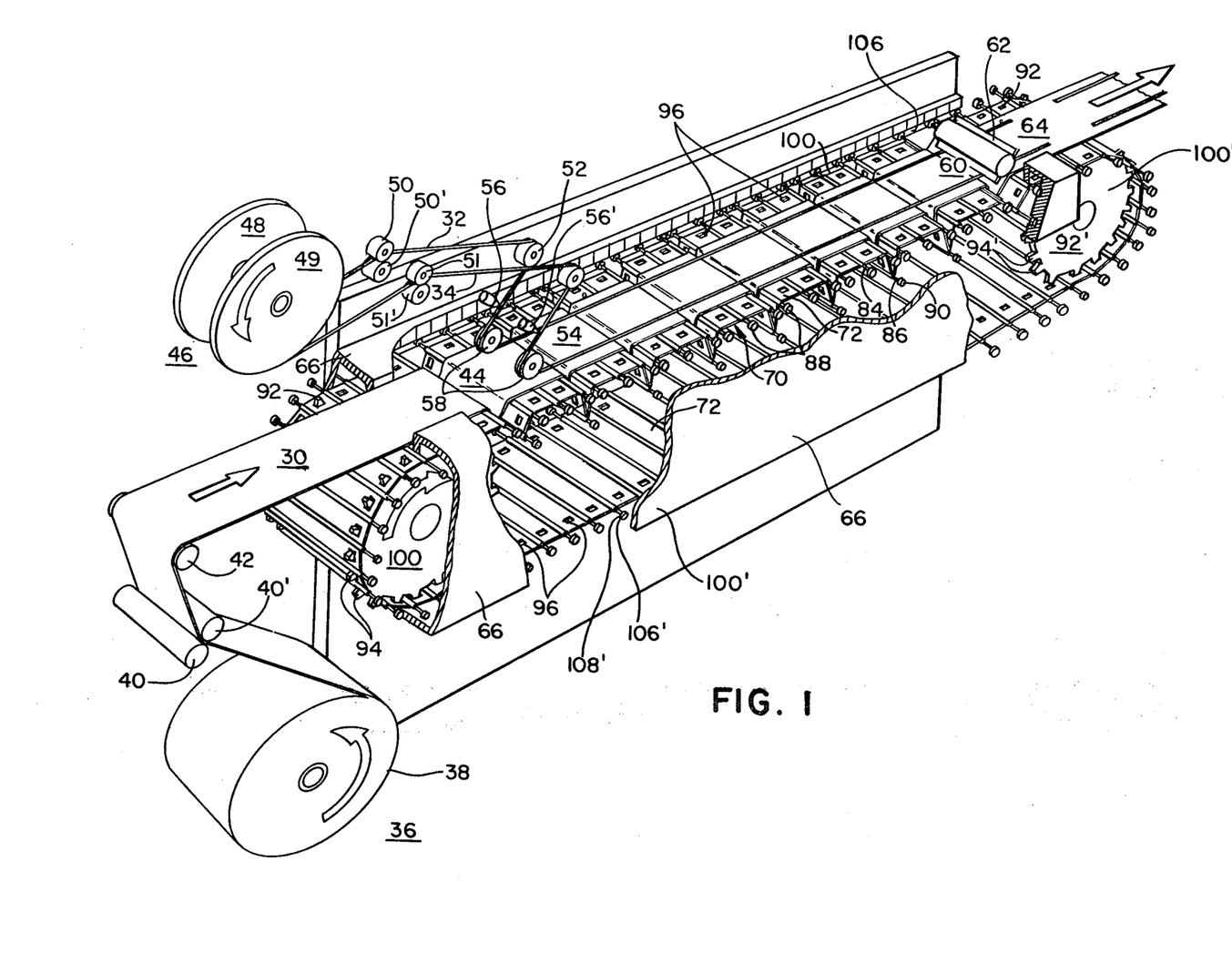
FIG. 1 is a simplified perspective view showing the web supply, elastic supply, web folding, elastic attaching, elastic cutting, and web unfolding stations of the diaper manufacturing apparatus of the invention.

Referring now to FIG. 1, apparatus is shown for supplying a web 30 and elastic ribbons 32 and 34, folding the web 30, attaching the ribbons 32 and 34 to the web 30, cutting the ribbons 32 and 34 opposite the locations of the folds, and unfolding the web 30. Apparatus for applying the absorbent pad 6, the waist fasteners 18 and 20, and the topsheet 2, all illustrated in FIG. 15, is not shown or described herein inasmuch as they form no part of the present invention and may be incorporated into the finished diaper by methods and apparatus that are well known in the art.

Figure 2:
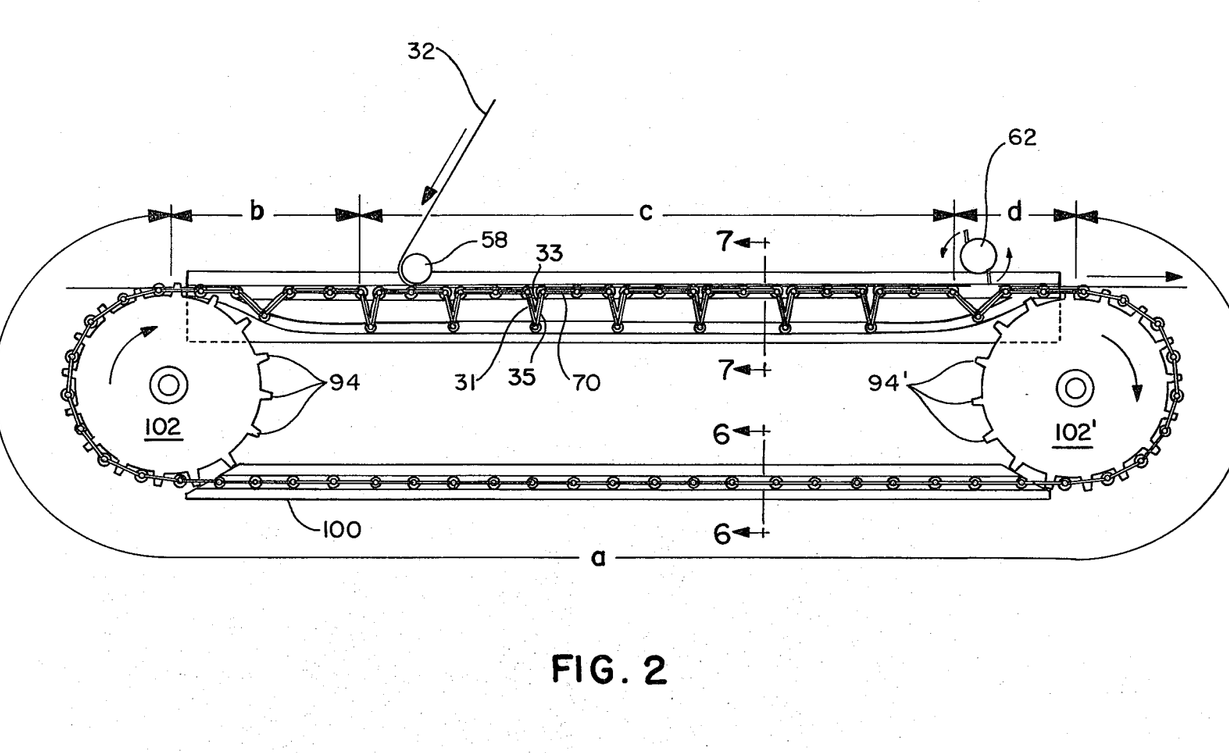
FIG. 2 is a simplified side elevation, cross-sectional view taken along section line 2—2 of FIG. 1.

Referring again to FIG. 1, there is shown a web supply station 36 at which the web material 30 is drawn from a supply roll 38 by feed rolls 40, 40' and, after passing over tension roll 42, the web 30 is fed to folding station 44 where it is moved into engagement with a continuously moving continuous articulated belt 70 and folded by the belt 70 to form fold pockets 31 having opposite ends 33 and 35 (see FIG. 2). The means for moving the web 30 into engagement with the belt 70 comprise the feed rolls 40, 40' and the tension roll 42. The tension roll 42 is positioned as shown in FIG. 1, such that the web 30 continuously moves into engagement with the belt 70. (see FIG. 2). A vacuum means 66 is positioned along the continuous belt 70 to hold the web 30 tightly against the belt 70. At the elastic ribbon supply station 46, the elastic ribbons 32 and 34 are drawn from supply rolls 48 and 49 by feed rolls 50, 50' and 51, 51'. The elastic ribbons 32 and 34 are then passed over a tension sensing roll 52 which, through feedback means (not shown), controls the speed of the feed roll 50, 50' and 51, 51' such that the elastic ribbons 32 and 34 are maintained under tension as they move with the web 30 through the elastic attaching station 54 and to an elastic cutting station 60. The effect of applying the elastic ribbons under tension is to elasticize those portions of the garment obtained from the web when the web is cut and the cut members are in a relaxed condition.

At the elastic ribbon attaching station 54, adhesive nozzles 56, 56' apply adhesive lines 26 and 28 respectively to the elastic ribbons 32 and 34 continuously along the lengths of the ribbons 32 and 34. Subsequent to the application of the adhesive lines 26 and 28 to the ribbons 32 and 34, the web 30 and the elastic ribbons 32 and 34 are moved together under a nip roll 58 which presses the elastic ribbons 32 and 34 against the unfolded portions of the web 30. The ribbons 32 and 34 are then cut opposite the folds in the web 30 by cutter 62 at cutting station 60, the web 30 is unfolded at unfolding station 64, and the continuous web 30 with spaced apart elastic strips 22 and 24 continues on to additional stations in the diaper producing apparatus.

Figure 3:
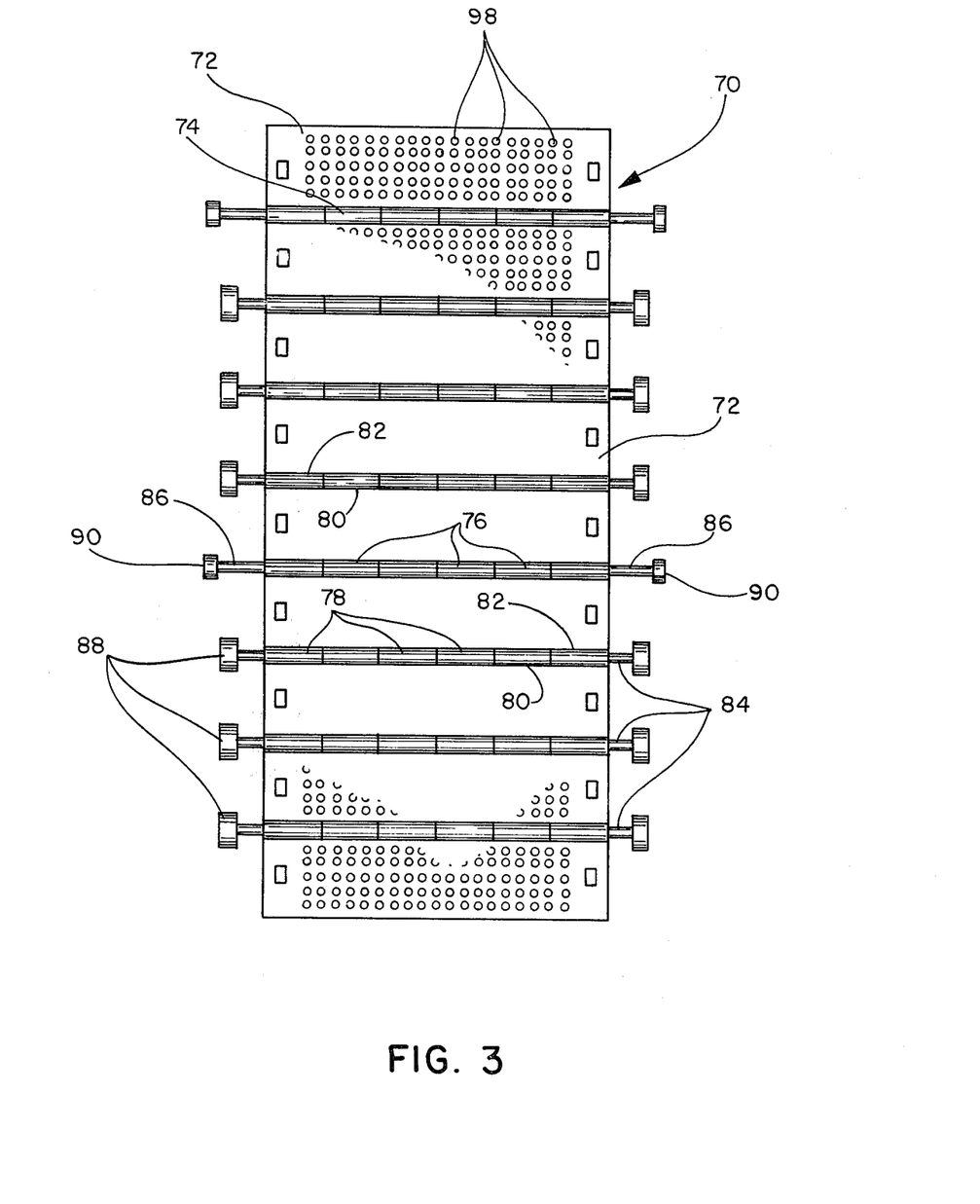
FIG. 3 is a plan view of a portion of the continuous articulated belt of the invention.

In FIGS. 2–5 and, in particular in FIG. 3, the continuous articulated belt 70 is illustrated as having a plurality of plate members 72 each connected to an adjacent plate member by pivotal joints or hinge means 74. Each of the plate members 72 has a plurality of vacuum openings 98 permitting the application of a vacuum means 66 through the members 72 to hold the web 30 against the members 72 during the engagement of the web 30 with the belt 70. Each of the hinge means 74 includes a first plurality of hollow cylindrical members 76 affixed to a plate member 72 at its edge 80 located adjacent another plate member 72 and a second plurality 78 of hollow cylindrical members affixed to the plate member 72 at its edge 82 adjacent another plate member 72. Each of the hinge means 74 also includes either a shaft member 84 or a shaft member 86 which passes through the hollow cylindrical members 76 and 78 of each two adjacent plate members 72 to permit the plate members 72 to pivot about the shafts. The hollow cylindrical members 76 and 78 of each pair of adjacent plate members 72 are aligned such that either the shaft 84 or the shaft 86 can readily pass through the members 76 and 78. Attached to the ends of the shafts 84 are cam followers or rollers 88 and attached to the end of the shafts 86 are cam followers or rollers 90.

In FIGS. 1 and 2, the continuous articulated belt 70 is shown being driven along a guide cam or track means 100, 100' respectively having cam grooves 106 and 108 and 106' and 108'. The drive source for belt 70 is two pair of drive sprocket wheels 92, 92' and 102, 102' respectively having a plurality of sprocket gear teeth 94, 94' fitting into sprocket openings 96 in the plate members 72 of the belt 70. The guide means 100 is identical in its operation to guide means 100' and the drive sprocket wheel pair 92, 92' are identical in their operation to sprocket wheels 102, 102'. Accordingly, only guide means 100 and drive sprocket wheels 92, 92' and their associated elements will hereafter be described.

Figures 5, 6, 7:
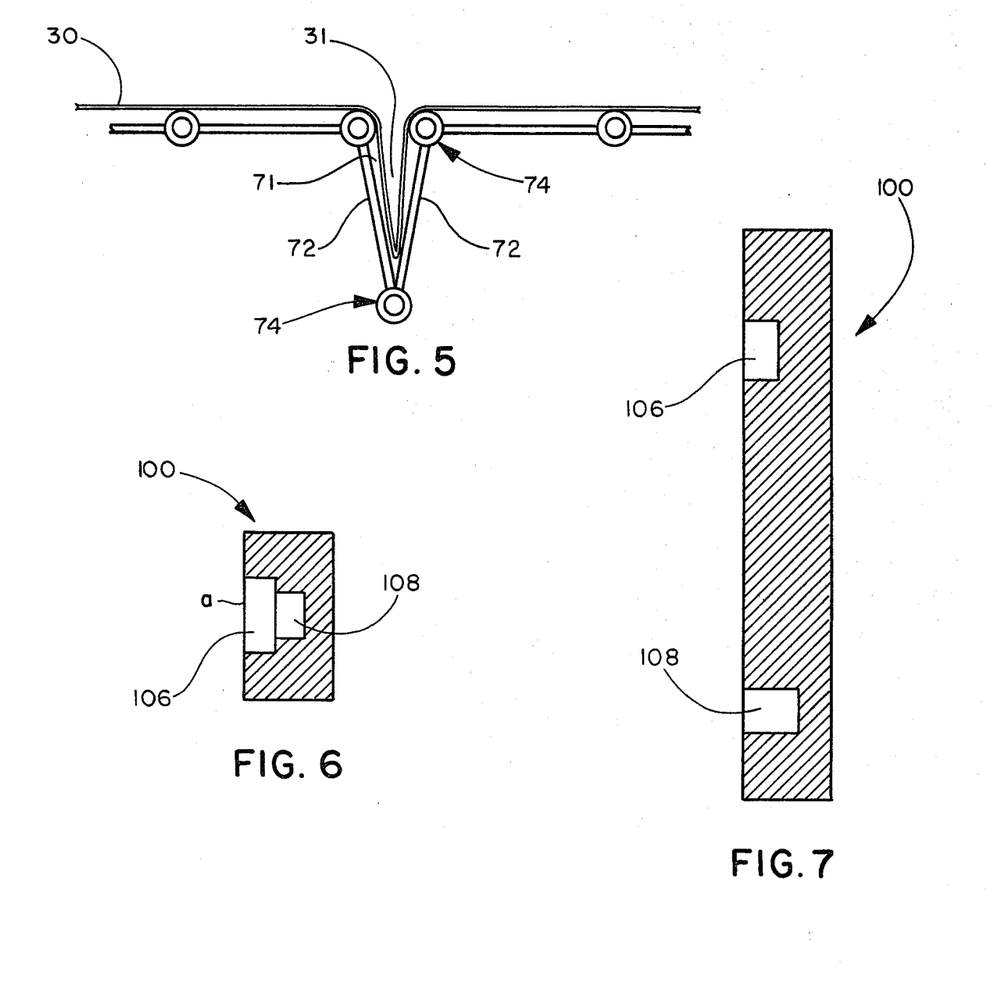
FIG. 5 is a simplified side elevation view of the continuous articulated belt of the invention shown in a folded position.
FIG. 6 is a cross-sectional view of the guide means of the invention showing the cam grooves for the different cam followers coinciding with each other.
FIG. 7 is a cross-sectional view of the guide means of the invention showing the cam grooves spaced apart from each other.

The guide track 100 has a first section a in which the cam grooves 106 and 108 are together and follow essentially the same path. In FIG. 6, the cam groove 108 is shown as being superimposed on the cam groove 106 along the first section a. The guide track 100 also includes section b in which the cam grooves 106 and 108 diverge from each other, a section c in which the cam grooves 106 and 108 run spaced and essentially parallel with each other, and a section d in which the cam grooves 106 and 108 converge toward each other to again follow the same path along section a. FIG. 7 illustrates a cross section through section c of guide track 100 showing the cam groove 106 and cam groove 108 in their spaced apart positions.

Figure 4:
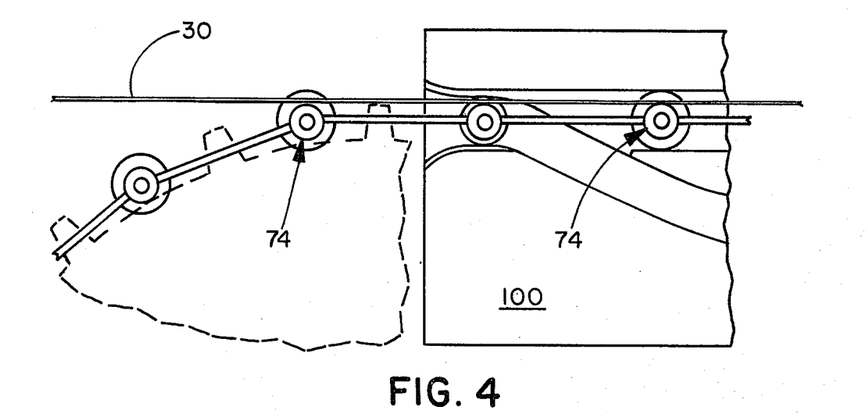
FIG. 4 is a simplified side elevation view of a portion of the continuous articulated belt of the invention in a relatively aligned position.

The cam rollers 90 on the end of shafts 86 have a slightly smaller diameter than the diameters of rollers 88 and extend further from the plate 72 than do rollers 88 so that the cam rollers 90 follow the cam grooves 108 along the guide track 100. The cam rollers 88 mounted on the shorter shafts 84 rest in the follow the cam grooves 106 as the belt 70 moves along the guide track 100. At the transition point where the hinge means 74 on the belt 70 travel from section a to section b of guide track 100, the cam grooves 106 and 108 move from a position following the same path to separate paths. The cam followers 88 and 90 will follow the grooves 106 and 108 to separate paths so that the plates 72 move from a position relatively in alignment with each other, as shown in FIG. 4, as they move from sprocket wheel 92' to sprocket wheel 92 and around sprocket wheel 92 to a folded position, as shown in FIG. 5, caused by the moving apart of the cam rollers 88 and 90. FIG. 2 shows a partial degree of folding of plate members 72 as the cam rollers 106 and 108 move along the diverging grooves 106 and 108, and a complete folding of plate members 72 in which the plate members 72 face each other and form fold spaces 31 as the cam rollers 88 and 90 move along section c of the guide track 100. In section d of the guide track 100, the plate members 72 are in an unfolding, partially folded mode caused by the converging of the cam grooves 106 and 108.

The drive rate of the sprocket wheels 92, 92' and 102 and 102' is constant. However, the belt 70 moves at the drive rate of the sprocket wheels only during its movement along section a of the guide means 100. At section b the rate of movement of the belt 70 decreases due to the folding of the plate members 72 and the speed of the belt 70 continues constant at a slower rate as the belt moves along section c of the guide means 100. At section d of the guide means 100, due to the unfolding and extension of the plate members 72, the belt 70 increases in its rate of movement back to the rate of the sprocket wheels 92, 92' and 102, 102'. The web 30 is moved into engagement with the belt 70 at or just prior to the beginning of section b of the guide means 100. The web 30 then moves at the same rate as the belt 70 as the latter moves along sections b, c, and d of the guide means 100 until the point where the web 30 moves out of engagement with the belt 70. Also, because the web 30 moves at the same speed as the belt 70 whether the speed of the belt 70 is varying or constant, and because the web 30 is held relatively tightly against the belt 70 by the vacuum means 66, the web 30 will not move relative to the web 70 while the web 30 is in engagement with the web 70. Thus there is no problem of undesired looseness or tightness of the web 30 or correct positioning (registration) of the web relative to the location of the diaper fabrication operations such as the location of the cut made on the elastic ribbons 32 and 34.

As previously discussed, the continuous elastic ribbons 32 and 34 which have been adhered to the folded web 30 at elastic ribbon attaching station 54 are cut opposite the fold pockets in the web 30 by the cutter 62 at cutting station 60. The cutter 62 may be any of several types which are well known in the art, including a rotating double edged cutter in which the cutting edge elements are electrically heated wires which provide a very rapid severing with little applied pressure to the elastic by the cutting edge. As shown in FIG. 2, the cutting of the ribbons 32 and 34 is preferably accomplished just after unfolding of the plate member 72 initiates so that there is sufficient room to make the cut without the hot cutting edges touching the web 30.

To summarize the operation of the apparatus and method, a continuous web 30 is fed into engagement with a moving, continuous articulated belt 70 and is held in engagement with plate members 72 of the belt 70 by a vacuum applied through openings 98 in plate members 72. As the conveyor belt 70 moves along the guide track 100, selected adjacent pairs of its plate members 72 are folded together to face each other by the action of cam followers 88 and 90 respectively attached to shafts 84 and 86 connecting the plate members 72 together. As the plate members 72 fold together, they also fold the web 70 to form spaced apart pockets 31 in the web. After the folding step is completed, continuous, moving elastic ribbons 32 and 34 are fed into engagement with the web 30 in the direction of its travel and are adhered to the web 30 such that the ribbons 32 and 34 are bonded only to the portions of the web 30 between fold pockets and bridge the fold pockets of the web 30. As the conveyor belt 70 moves toward section d of the guide track 100, the folded plate members 72 are caused to unfold by the convergence of cam grooves 106 and 108 in the guide track means 100. As the unfolding of the plate members 72 and therefore the fold pockets in the web 30 initiates, the continuous elastic ribbons 32 and 34 are severed to thereby provide spaced apart, separate elastic strips 22 and 24 along the length of the web 30. The web 30 then exits the apparatus while the plate members 72 unfold to a substantially aligned position and rotate around the sprocket wheels 92' and 102' to return to the web fold station 44.

Figures 8, 9, 10:
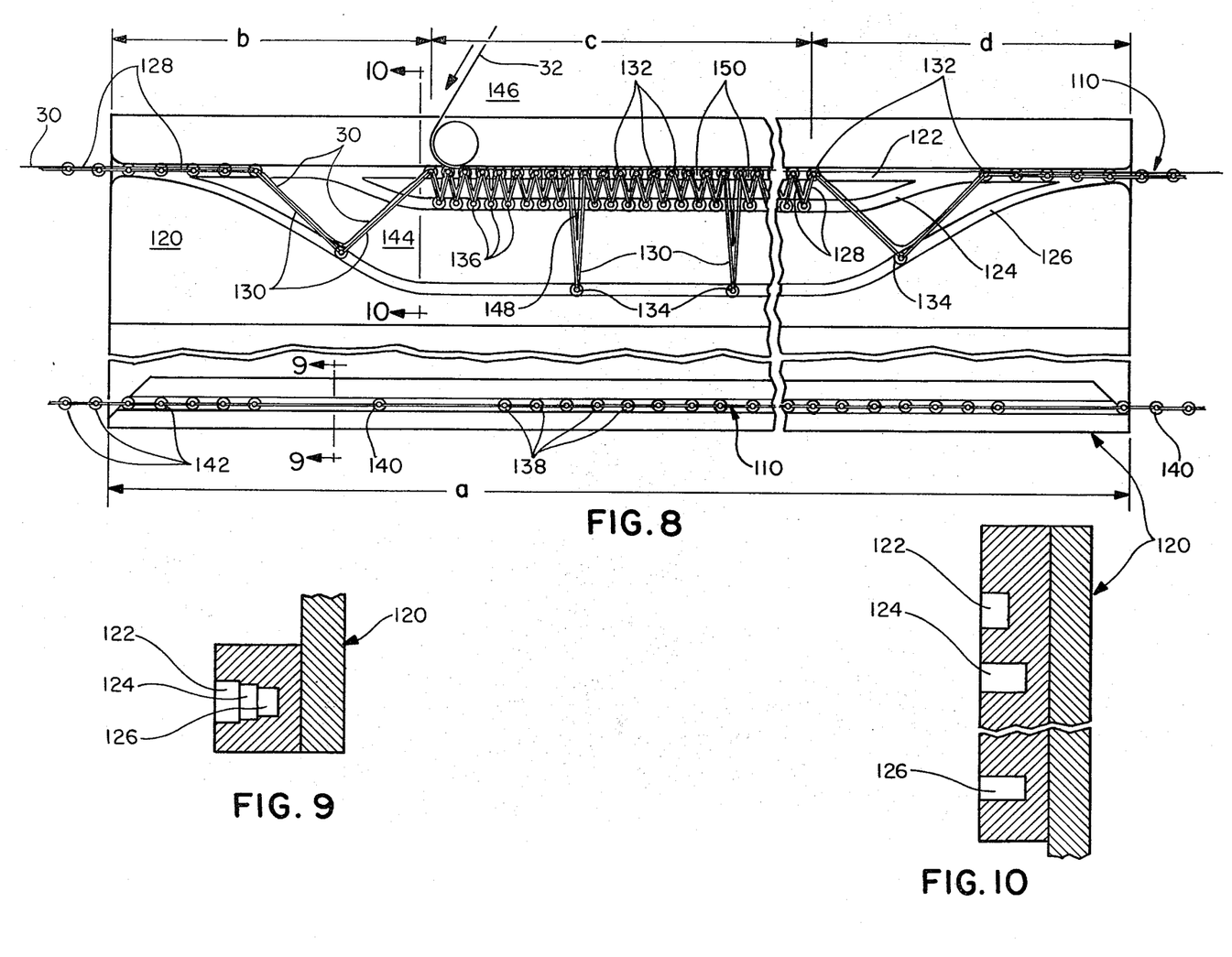
FIG. 8 is a simplified side elevation, cross-sectional view of an alternative embodiment of the invention illustrating the guide means and continuous articulated belt in a folded condition.
FIG. 9 is a cross-sectional view of the guide means of FIG. 8 showing the cam grooves in a position coinciding with each other.
FIG. 10 is a cross-sectional view of the guide means of FIG. 8 showing the cam grooves in a position spaced apart from each other.

The principals of the present invention shown in FIGS. 1-7 may be utilized in modifications of the invention and, in FIGS. 8-10, there is illustrated an alternative embodiment of the invention utilizing these principals. In FIGS. 8-10, elements of the apparatus which are the same as shown in FIGS. 1-7 carry the same identifying numerals. With reference to FIGS. 8-10, the apparatus is shown as having a continuous articulated belt 110 supported by and moving along a guide track means 120. The guide means 120 includes cam grooves 122, 124 and 126. The belt 110 includes narrow plate members 128, wide plate members 130, and pivotal joints 132, 134 and 136. The narrow plate members are connected to each other by the pivotal joints 132 and 136. The wide plate members 130 are connected to each other by the pivotal joints 134 and each of the wide plate members 134 is connected to the most adjacent narrow plate member 128 by a pivotal joint 132. While the belt 110 is moving along the portion of section a of the guide track means 120 shown in FIG. 8, the cam followers 1388, 140 and 142 of pivotal joints 132, 134 and 136, respectively, will be traveling essentially in alignment with each other in the position of the cam grooves as shown in FIG. 9. While the belt 110 is traveling along section c of the guide means 120, the pivotal joints 132, 134 and 136 will be traveling spaced apart from each other along the cam grooves 122, 124 and 126 in their positions as shown in FIG. 10. Similarly to the embodiment shown in FIGS. 1–7, as the belt 110 moves along sections b and d of guide means 120 the cam grooves 122, 124 and 126 are in a diverging or converging transition stage. As shown in FIG. 8, while the belt moves along the web folding station 144 and elastic application station 146, and as the cam grooves are diverging from each other, the web 30 will have a major fold pocket 148 formed by the wide plate members 130 and minor fold pockets 150 formed by the narrow plate members 128. The major fold pockets 148 in the web 30 correspond to the waist area in the finished diaper, as shown in FIG. 15, in which it is desired not to have elastic strips 22 and 24. The minor fold pockets 150 correspond to the leg areas 14 and 16 in the finished diaper. Continuous elastic ribbons 32 and 34 are applied to the web 30 at the elastic attaching station 146 across and spanning both the major fold pockets 146 and the minor fold pockets 150, in a manner similar to that described with respect to the embodiment shown in FIGS. 1–7. However, elastic ribbons 32 and 34 are not maintained in tension as they are applied but, rather, are applied in a relatively relaxed condition. Thus, subsequent to severing of the elastic ribbons 32 and 34 opposite the major fold pockets 150 and the unfolding of the web, the elastic strips 22 and 24 will be elongated due to the unfolding of the minor fold pockets 150 thereby elasticizing the leg areas 14 and 16 of the finished diaper and biasing the leg areas toward a retracted condition when the web 30 is cut to form the finished diaper.

Figures 11, 12, 13:
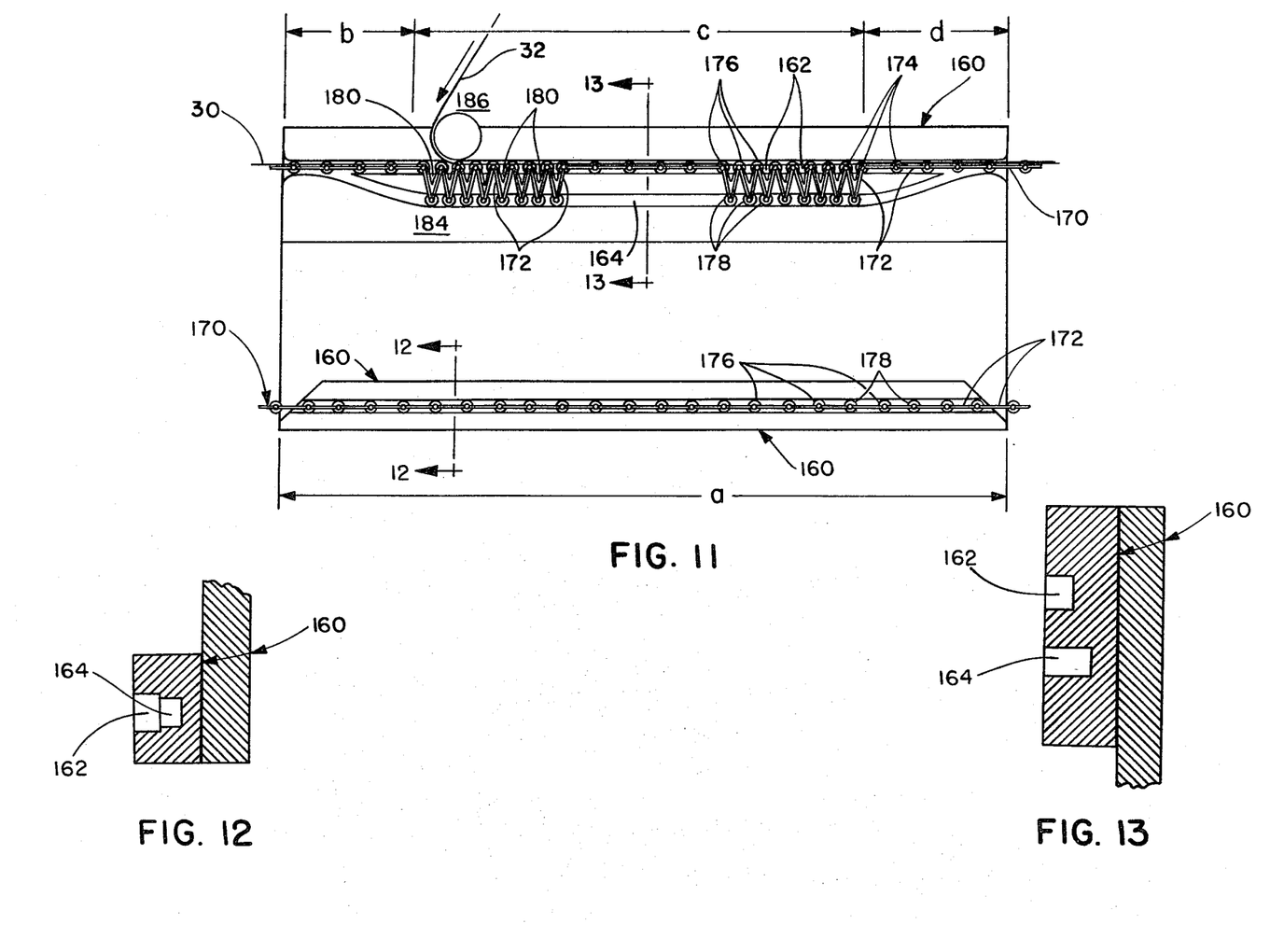
FIG. 11 is a simplified side elevation, cross-sectional view of another alternative embodiment of the invention illustrating the guide means and continuous articulated belt in a folded condition.
FIG. 12 is a cross-sectional view of the guide means of FIG. 11 showing the cam grooves in a coinciding position.
FIG. 13 is a cross-sectional view of the guide means of FIG. 11 showing the cam grooves in a spaced apart position.

In a third embodiment of the invention, shown in FIGS. 11–13, a guide track means 160 having cam grooves 162 and 164 guides and supports a continuous articulated belt 170 comprising plate members 172 and pivotal joints 174. In the portion of section a of the guide track means shown in FIG. 11, the cam grooves 162 and 164 are aligned as shown in FIG. 12 and the cam followers 176 and 178 attached to the pivotal joints 174 move essentially in alignment with each other as the belt 70 travels along section a. As the belt 170 moves along section c of the guide track means 160 in which the cam grooves 162 and 164 are separated as shown in FIG. 13, the cam followers 176 follow a path correspondingly separated from the cam followers 178 to thereby cause the plate members 172 to fold and form fold pockets 180 in the web 30. The fold pockets 180 are formed only in the portion of the web 30 that corresponds to the leg areas 14 and 16 in a finished diaper and are relatively small such that they appear as pleats in the web 30. The continuous elastic ribbons 32 and 34 are applied at the elastic application station 186 in an untensioned condition so that, upon unfolding of the fold pockets 180 to thereby straighten the web 30 and the leg areas 14 and 16, an elasticization effect is achieved in the leg areas 14 and 16. The ribbons 32 and 34 are not severed, as in the previously described embodiment, to eliminate elastic from the waist section of the finished diaper. Rather, the finished diaper will have elastic ribbon adhered continuously along its length, however, the elastic ribbon will be relaxed in the waist area so that it will have no elasticization effect in the waist area and only the leg areas 14 and 16 will be elasticized.

An apparatus and a method is thus provided for elasticizing only the leg areas of a disposable diaper by folding the web from which the diaper is formed at appropriate locations along the length of the web and bonding elastic to the web across the folds. A folded portion of the web may, after cutting of the elastic ribbon opposite the folded portion, constitute the waist area of a finished diaper. On the other hand, the area of the web in which a plurality of folds are made to provide a pleating effect may constitute the leg area of the finished diaper which is elasticized by the contraction effect of the elastic when the small folds in the leg areas are extended. Also, the elastic may be applied in a relaxed condition so that there is no elasticization effect in the waist area and an elasticization effect is achieved only in the leg area due to the small folds formed in the part of the web corresponding to the leg area in a finished diaper.

It will be understood that the foregoing description of the present invention is for purposes of illustration only and that the invention is susceptable to a number of modifications or changes, none of which entail any departure from the spirit and scope of the present invention as defined in the hereto appended claims.

What is claimed is:

1. In an apparatus for manufacturing elastic leg disposable diapers including means for continuously moving a web of material in the direction of its length into engagement with a folding means and means for continuously moving elastic ribbon into engagement with the web, the combination wherein:

the folding means comprises moving articulated means with which the web is brought into engagement, the moving articulated means engaging and holding the web immobile relative to the articulated means along the entire length of the web engaging the articulated means for forming fold pockets in the web;

guide means for causing said articulated means to move from a relatively aligned condition to a folded condition in which the articulated means has fold spaces whereby the fold pockets are formed in the web;

means for moving the elastic ribbon to a position in engagement with the web and spanning said fold pockets; and means for adhering the elastic ribbon to the web at positions other than along the fold pockets of the web.

2. The combination according to claim 1 wherein:

the web has predetermined areas supported by the articulated means and the fold pockets are between the predetermined areas;

the adhering means adheres the elastic ribbon to the predetermined areas of the web; and further comprising means for severing the elastic ribbon opposite said fold pockets.

3. The combination according to claim 1 wherein:

the web has predetermined areas supported by the articulated means and corresponding to waist areas of finished diapers;

the articulated means forms a plurality of fold pockets in the web between each pair of predetermined areas, the plurality of fold pockets between a pair of predetermined areas corresponding to the leg area of a finished diaper;

the elastic ribbon is adhered in a relatively relaxed condition to the web between each fold pocket of the plurality of fold pockets and to each predetermined area; and further comprising means for simultaneously severing the elastic ribbon and the web transversely across each predetermined area of the web.

4. The combination according to claim 1 wherein:

the articulated means forms a plurality of fold pockets in the web, each fold pocket having a depth in a direction perpendicular to the length of the web, selected ones of said fold pockets being uniformly spaced apart from each other and separated by a plurality of the other fold pockets, said selected ones of the fold pockets having a greater depth than the depth of the other fold pockets;

the elastic ribbon being adhered to the web in a relatively relaxed condition and between each one of the fold pockets in the web; and further comprising means for severing the elastic ribbon opposite said selected ones of the fold pockets.

5. The combination according to claim 1, 2, 3 or 4 wherein:

the articulated means is a continuous belt comprising a plurality of plates each having two of its opposing edges pivotally joined to another plate; and the guide means causes selected adjacent pairs of said plates to pivot to a facing position so that the articulated means is in said folded condition and the facing plates form the fold pockets.

6. The combination according to claim 5 wherein:

the continuous belt includes hinge means pivotally joining each plate to another plate and cam follower means connected to each hinge means;

the pairs of adjacent plates, when in a facing position, have an open end and a closed end; and the guide means having a first cam groove in which the cam followers at the open end of the pairs of adjacent plates are mounted and at least two second cam grooves in one of which the cam followers at the closed end of the pairs of adjacent plates are mounted.

7. The combination according to claims 1, 2 or 3 wherein:

the articulated means is continuously moving; and the articulated means and web have an initial location of engagement and the articulated means and web move at the same speed at such initial location.

8. The combination according to claim 1 further comprising vacuum means positioned along the moving articulated means for holding the web in engagement with the articulated means.

9. In an apparatus for manufacturing elastic leg disposable diapers including means for continuously moving a web of material in the direction of its length into engagement with folding means and means for continuously moving elastic ribbon into engagement with the web, the combination wherein:

the folding means comprises moving articulated means with which the web is brought into engagement, the moving articulated means engaging the web along its length for forming fold pockets in the web, the articulated means being the sole means engaging the fold pockets of the web;

guide means for causing said articulated means to move from a relatively aligned condition to a folded condition in which the articulated means has fold spaces whereby the fold pockets are formed in the web;

means for moving the elastic ribbon to a position in engagement with the web and spanning said fold pockets; and means for adhering the elastic ribbon to the web at positions other than along the fold pockets of the web.

10. The combination according to claim 9 further comprising vacuum means positioned along the moving articulated means for holding the web in engagement with the articulated means.

11. A method for manufacturing elastic leg disposable diapers wherein a web of material is moved continuously in the direction of its length and elastic ribbon is continuously moved into engagement with the web, comprising the steps of:

moving articulated belt means continuously in the direction of the length of the web;

moving the web into engagement with the belt means;

folding the belt means and web together to form folded pockets in the web;

adhering the elastic ribbon to the web at areas between the folded pockets; and severing the elastic ribbon opposite the folded pockets.

12. The method according to claim 11 wherein the belt means comprises a plurality of hinges connecting a plurality of belt members and wherein the step of folding the belt means is accomplished by moving alternating ones of said hinges along spaced apart paths.

13. The method according to claim 11 wherein the web and the belt means, when engaged, do not move relative to each other.

14. The method according to claim 11 further comprising the step of applying vacuum pressure to the web to hold it in engagement with the belt means.

* * * * *